US008012767B2

(12) United States Patent
Rasnow et al.

(10) Patent No.: US 8,012,767 B2
(45) Date of Patent: Sep. 6, 2011

(54) PIPETTE TIP LOADING ASSEMBLY

(75) Inventors: Brian Rasnow, Newbury Park, CA (US); Chuck Z. Li, Thousand Oaks, CA (US); Stephen Robert Wilson, Glen Iris (AU)

(73) Assignee: Amgen Inc., Thousand Oaks, CA (US)

( * ) Notice: Subject to any disclaimer, the term of this patent is extended or adjusted under 35 U.S.C. 154(b) by 1279 days.

(21) Appl. No.: 11/500,174

(22) Filed: Aug. 7, 2006

(65) Prior Publication Data
US 2008/0031781 A1 Feb. 7, 2008

(51) Int. Cl.
*G01N 1/10* (2006.01)
*B01L 3/02* (2006.01)

(52) U.S. Cl. ......... 436/180; 422/501; 422/524; 422/525

(58) Field of Classification Search ............ 422/99–100, 422/63–68.1, 500–501, 524–525; 436/180
See application file for complete search history.

(56) References Cited

U.S. PATENT DOCUMENTS

| | | | |
|---|---|---|---|
| 5,470,538 A | 11/1995 | Lind | |
| 5,622,676 A | 4/1997 | Lind | |
| 5,996,818 A * | 12/1999 | Boje et al. ...................... | 211/74 |
| 6,019,225 A | 2/2000 | Kalmakis et al. | |
| 6,098,802 A * | 8/2000 | Asa et al. ...................... | 206/443 |
| 6,247,891 B1 | 6/2001 | Lind | |
| 6,589,483 B1 * | 7/2003 | Maeda .......................... | 422/100 |
| 6,666,644 B1 | 12/2003 | Lind et al. | |
| 2002/0168300 A1 | 11/2002 | Bramwell et al. | |
| 2003/0017604 A1 | 1/2003 | Hitch et al. | |
| 2004/0208795 A1 * | 10/2004 | Toi et al. ...................... | 422/100 |
| 2004/0231438 A1 | 11/2004 | Schwartz | |
| 2005/0082243 A1 * | 4/2005 | Lahti et al. ..................... | 211/74 |
| 2005/0265900 A1 | 12/2005 | Gard et al. | |

OTHER PUBLICATIONS

PCT International Search Report from PCT/US2007/074855, dated Jan. 8, 2008.

* cited by examiner

*Primary Examiner* — Brian R Gordon
(74) *Attorney, Agent, or Firm* — Vierra Magen Marcus & DeNiro LLP

(57) ABSTRACT

A method of loading a plurality of pipette tips on a plurality of mandrels of a pipetter is provided. A plurality of pipette tips are inserted in a plurality of receptacles of a tip loading assembly. The plurality of pipette tips are oriented with respect to each other by a plate. The tip loading assembly includes, but is not limited to, an insertion surface. The insertion surface includes the plurality of receptacles configured to accept the plurality of pipette tips. A receptacle from among the plurality of receptacles includes a receptacle wall and a beveled surface that extends from at least a portion of the insertion surface. A retention force is applied to the plate. The plurality of pipette tips are attached to a plurality of mandrels of a pipetter and are separated from the plate.

2 Claims, 9 Drawing Sheets

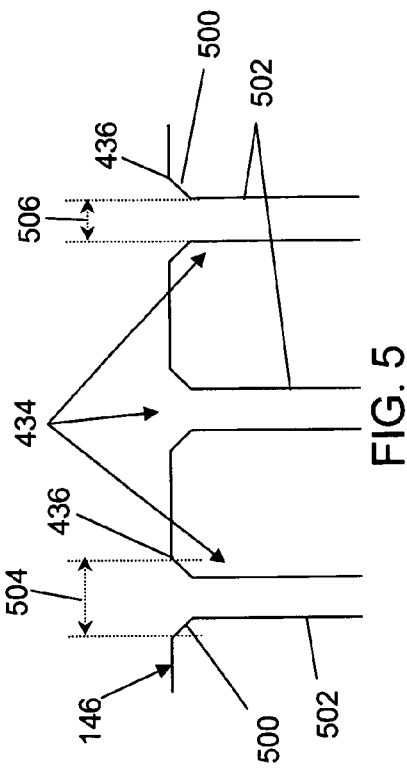
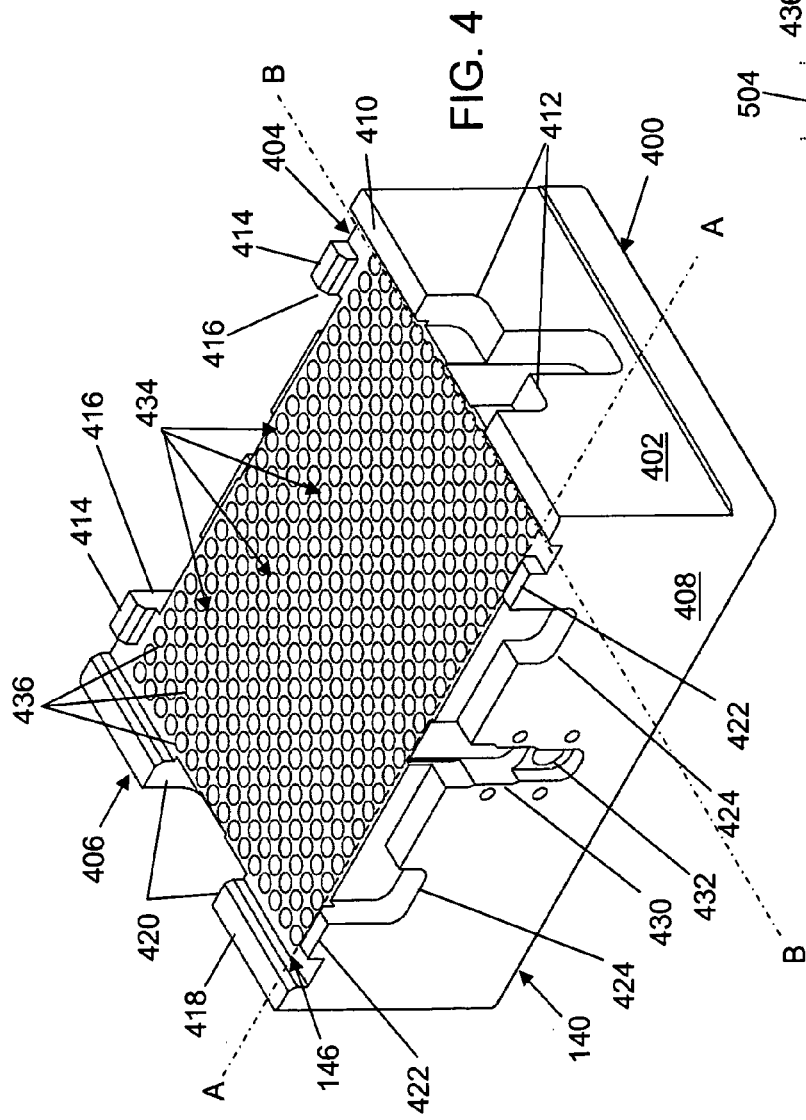

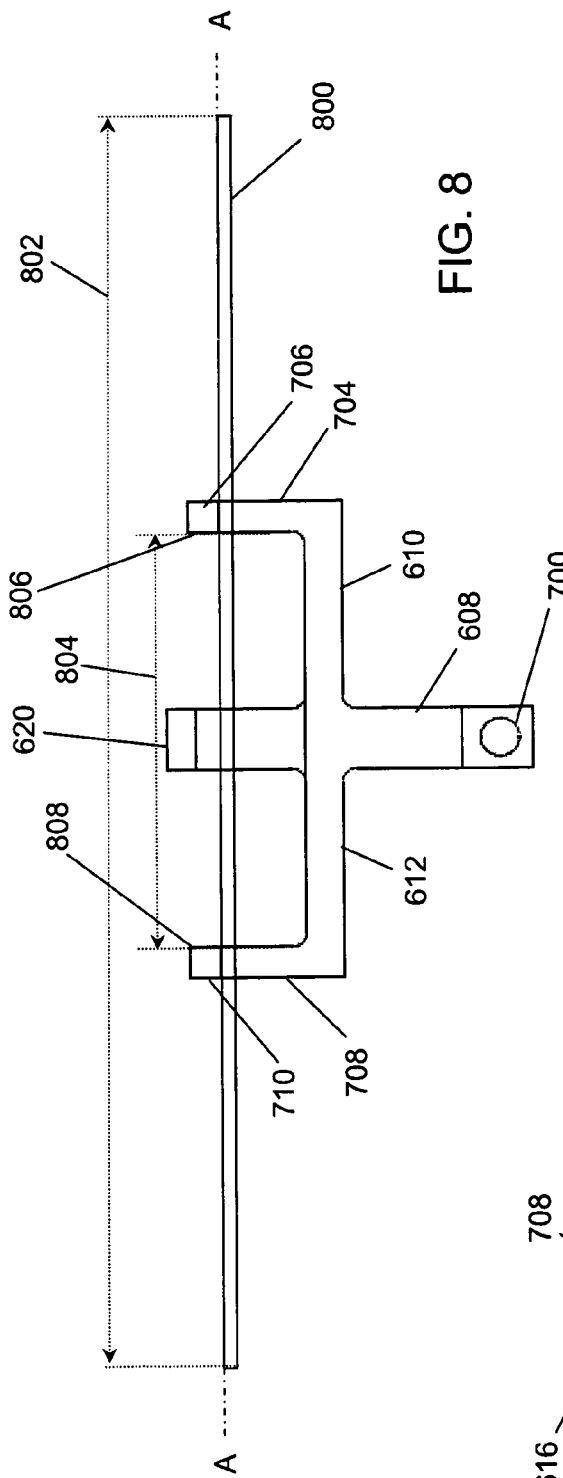
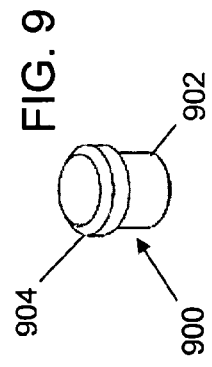
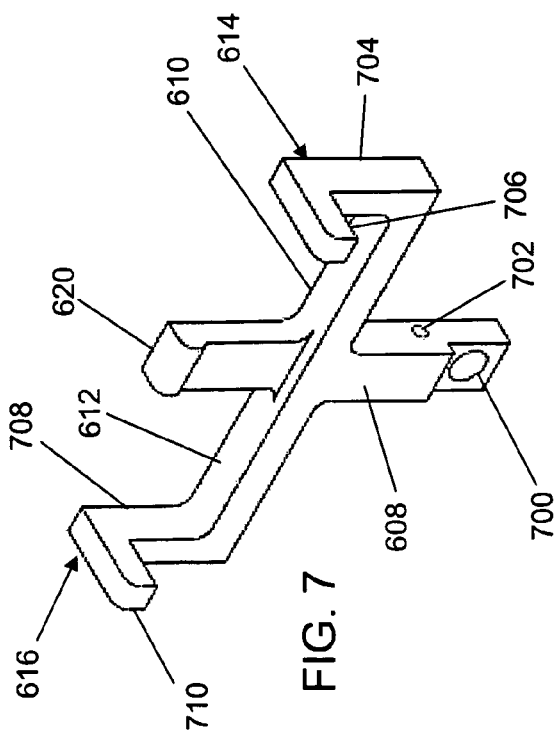
FIG. 8
FIG. 9
FIG. 7

PIPETTE TIP LOADING ASSEMBLY

FIELD OF THE INVENTION

The subject of the disclosure relates generally to a variety of instruments that utilize pipette tips. More specifically, the disclosure relates to an improved device for loading pipette tips onto a pipetter.

BACKGROUND OF THE INVENTION

The manipulation of chemical and/or biological materials in a laboratory environment has become increasingly automated in order to increase the throughput of the analyses executed by the equipment, to reduce the costs of manual labor in the laboratory, to increase the reliability of the analyses, and to reduce the exposure of laboratory workers to contact with hazardous chemical and/or biological materials. As a result, robotic arms have been incorporated into instruments to transport objects during the conduct of experiments in order to support the higher throughput and unattended processing time for the experiments. A common step in many of these experiments involves fluid manipulation such as pipetting, diluting, dispensing and aspirating of fluids. A device commonly used for the performance of fluid manipulation in an automated system is a multi-channel pipetter.

A typical pipette tip is formed with a substantially conical head and a frustoconical body. The tip head, which mates with the pipetter head, forms an opening at its proximal end while the body forms a smaller opening at its distal end. The pipette tip head has a larger outer diameter than the pipette tip body and forms an annular lower edge at the junction of the head to the body. In use, the head of the pipette tip is typically force fit onto the shaft of another device, such as a pipetter, and held in place by friction. The pipetter is operated to draw liquid into and to expel liquid from the pipette tip through the distal opening in the tip body.

In general, automated instruments utilizing multi-channel pipettors use replaceable tips to minimize the probability of carry-over and contamination while transferring compounds, proteins, DNA, RNA, cells, blood and other fluids between microtiter plates. Thus, during the conduct of experiments, pipette tips are repeatedly placed on pipettors and used to aspirate and to dispense liquids. Typically, the pipette tips are placed on a pipette tip head of an automated pipetter instrument and inserted into a number of wells of industry standard multi-well plates. The robotic pipetter instrument positions the pipette tips into the wells of the plate, and liquid is aspirated from the wells and into the pipette tips. Alternatively, liquid is dispensed from the pipette tips and into the wells. As a result, pipette tips are normally sold packaged in flats or racks which hold the tips in a standard arrangement for placement on pipette tip heads and insertion into the wells of multi-well plates.

For example, two common pipette tip arrangements include 96 or 384 pipette tips. Typically, the pipette tip heads are inserted into a number of apertures of a pipette tip holding card with the positioning of the pipette tips and apertures chosen to be compatible with a standard 96 or 384 multi-well plate. For example, the standard 96 aperture pipette tip rack and flat has a rectangular upper surface that defines an 8×12 array of 96 receptacles with approximately 9 millimeters separating the centers of adjacent receptacle apertures. Each aperture of the card has a diameter larger than the outer diameter of the pipette tip body, but smaller than the diameter of the annular lower edge of the pipette tip head. To store a pipette tip in the rack or flat, the body of the pipette tip is inserted into one of the receptacles, and the annular lower edge of the pipette tip engages the upper surface of the rack or flat. The pipette tip then rests within the receptacle with the head of the tip extending above the upper surface of the rack or flat and the body of the tip extending below the upper surface.

One of the most error-prone steps in automated pipetter instruments occurs during attachment of the pipette tips onto the head of the multi-channel pipetter. For example, a malfunction of an automated system incorporating a multichannel pipetter results when a tip holding card of a pipette tip flat remains attached to some or all of the pipette tips after attachment to a pipetter head. The malfunction may result when even a minor misalignment between any one of the pipette tips and the pipetter head occurs, or when the pipette tip flat includes any defectively manufactured tip or is itself defectively manufactured. The resulting malfunction can result in a failure to transfer fluid and may lead to a robot crash requiring human intervention and jeopardizing the original intent of unattended operation. Tight manufacturing tolerances for the pipette tips and pipette flats have not sufficiently resolved the problem. Therefore, what is needed is a tip loading assembly having increased tip loading reliability and reduced failure modes. This and other benefits are provided by the present invention as described herein below.

SUMMARY OF THE INVENTION

An exemplary embodiment provides a tip loading assembly. The provided tip loading assembly includes a number of improvements that increase the reliability of the tip loading process thereby permitting uninterrupted pipetter processing for extended time periods. Pipette tips are more easily inserted into a tip depot using receptacles having a beveled surface. Wider retainer clips and a stronger biasing member provide an increased retention force to hold a plate in place after attachment of the tips to the pipetter. A clamping module ensures that the tip depot remains in the proper position and orientation before, during, and after tip attachment.

In an exemplary embodiment, a tip loading assembly is provided. The tip loading assembly includes an insertion surface. The insertion surface includes a plurality of receptacles configured to accept a pipette tip. A receptacle of the plurality of receptacles includes a beveled surface that extends from at least a portion of the insertion surface.

In another exemplary embodiment, a pipetter instrument is provided. The pipetter instrument includes, but is not limited to, a pipetter, a tip loading assembly, and a controller. The pipetter includes, but is not limited to, a plurality of mandrels. The tip loading assembly includes an insertion surface. The insertion surface includes a plurality of receptacles configured to accept a pipette tip. At least one of the plurality of receptacles includes a beveled surface that extends from at least a portion of the insertion surface. It is particularly beneficial that receptacle(s) distal from the center of the insertion surface have such a beveled surface. Preferably, each receptacle of the plurality of receptacles includes such a beveled surface that extends from at least a portion of the insertion surface. The controller operably couples to the pipetter and sends a movement command to the pipetter to load a plurality of pipette tips inserted in the plurality of receptacles onto the plurality of mandrels.

In yet another exemplary embodiment, a method of loading a plurality of pipette tips on a plurality of mandrels of a pipetter is provided. A plurality of pipette tips are inserted in a plurality of receptacles of a tip loading assembly. The plurality of pipette tips are oriented with respect to each other by a plate, a tip holding card, tray, cassette, rack, or the like. The tip loading assembly includes an insertion surface. The insertion surface includes a plurality of receptacles with each receptacle configured to accept a pipette tip. Each receptacle of the plurality of receptacles includes a beveled surface that extends from at least a portion of the insertion surface. A retention force is applied to the plate. The plurality of pipette tips are attached to a plurality of mandrels of a pipetter and are separated from the plate.

Other principal features and advantages of the invention will become apparent to those skilled in the art upon review of the following drawings, the detailed description, and the appended claims.

BRIEF DESCRIPTION OF THE DRAWINGS

Exemplary embodiments will hereafter be described with reference to the accompanying drawings, wherein like numerals will denote like elements.

FIG. 4 is a perspective view of a tip depot of the tip loading assembly of FIG. 2 in accordance with an exemplary embodiment.

FIG. 5 is a side cross sectional view of an insertion surface of the tip depot of FIG. 4 in accordance with an exemplary embodiment.

FIG. 7 is a perspective view of a retainer clip in accordance with an exemplary embodiment.

FIG. 8 is a side view of the retainer clip of FIG. 7 in accordance with an exemplary embodiment.

FIG. 9 is a perspective view of a pivot pin in accordance with an exemplary embodiment.

DETAILED DESCRIPTION OF THE EXEMPLARY EMBODIMENTS

Figure 1:
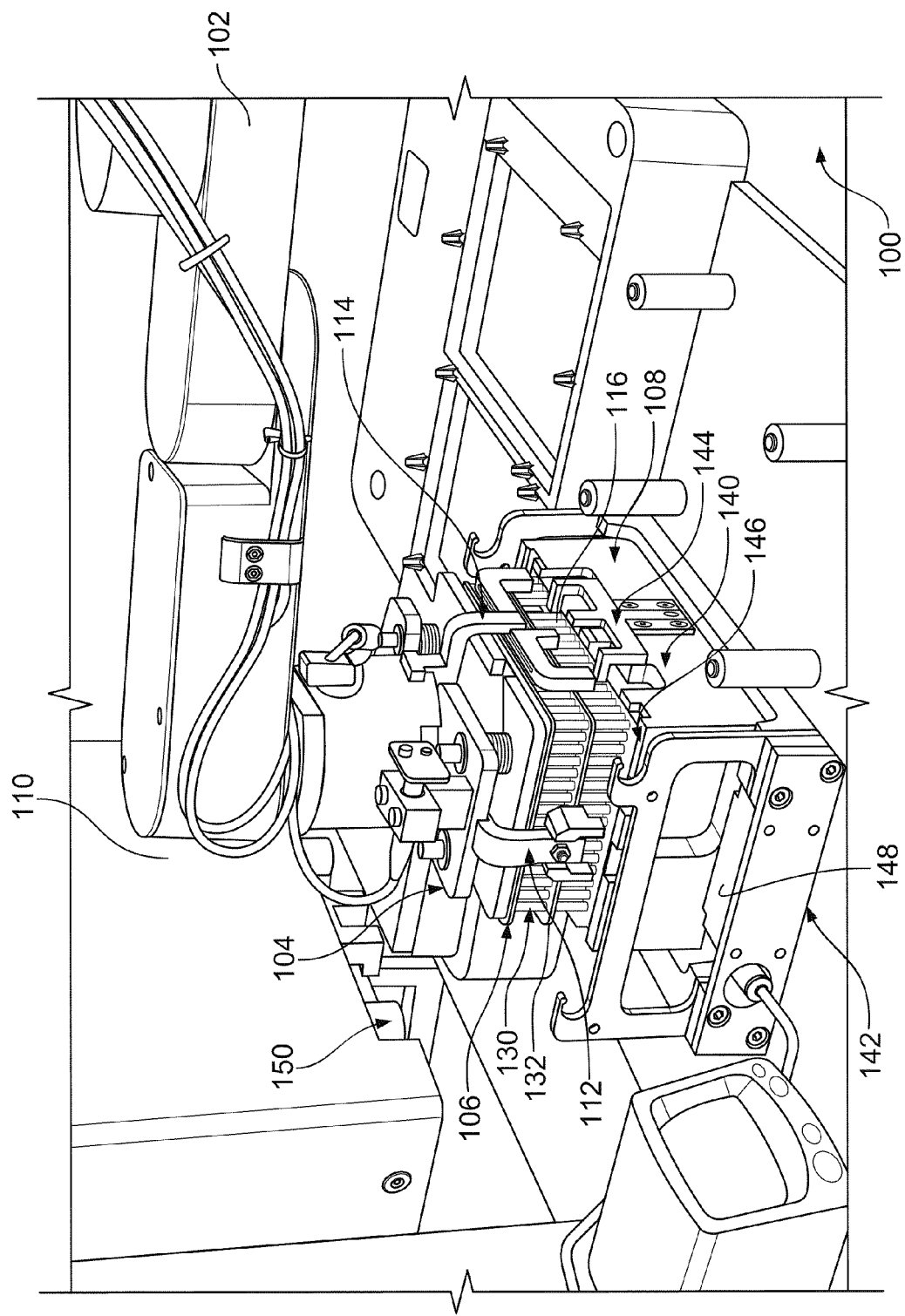
FIG. 1 is a perspective view of a pipetter instrument in accordance with an exemplary embodiment.

With reference to FIG. 1, a pipetter instrument 100, in accordance with an exemplary embodiment, is shown. Pipetter instrument 100 may be any of a variety of laboratory instruments as known to those skilled in the art both now and in the future without limitation. For example, pipetter instrument 100 may be a pipetting workstation, a compound plate replication platform, an assay workstation, a plate reader, a detector, or the like. Pipetter instrument 100 may include a controller (not shown), a robotic arm 102, a gripper 104, a pipette tip flat 106, a tip loading assembly 108, and a pipetter 110. Pipetter instrument 100 may include fewer or additional components as known to those skilled in the art.

In an exemplary embodiment, the controller includes a computer of any form factor executing one or more program implemented in software, hardware, and/or firmware to control robotic arm 102, gripper 104, tip loading assembly 108, and/or pipetter 110. As a result, the controller may interface with and control robotic arm 102, gripper 104, tip loading assembly 108, and/or pipetter 110 as known to those skilled in the art both now and in the future. In alternative embodiments, there may be a plurality of controllers.

In the exemplary embodiment of FIG. 1, robotic arm 102 is a multi-link structure providing movement of gripper 104 about a plurality of axes. Robotic arm 102 can be any suitable robotic arm including, but not limited to, a KiNEDx-series (Peak Robotics Inc., Colorado Springs, Colo.) robotic arm, a Trx (AB Controls, Inc., Irvine Calif.) robotic arm, or the like.

In the exemplary embodiment of FIG. 1, gripper 104 includes a first gripper arm 112, a second gripper arm 114, a third gripper arm (not shown), and a fourth gripper arm (not shown). Gripper 104 mounts to robotic arm 102. As used in this disclosure, the term "mount" includes join, unite, connect, associate, insert, hang, hold, affix, attach, fasten, bind, paste, secure, bolt, screw, rivet, solder, weld, and other like terms. The orientation at which gripper 104 mounts to robotic arm 102 is exemplified as vertical in FIG. 1. Mounting of gripper 104 to robotic arm 102, however, can be in any suitable orientation that enables the desired translational and/or rotational motion of gripper 104. Gripper 104 may include an actuator (not shown) that controls movement of one or more actuator jaw. Exemplary actuators include an electric motor, a servo, stepper, or piezo motor, a pneumatic actuator, a gas motor, or the like. At least one of first gripper arm 112, second gripper arm 114, the third gripper arm, and the fourth gripper arm is mounted to the one or more actuator jaw such that the actuator can move at least one of the gripper arms. Gripper 104 may be capable of supporting one or more types of object. For example, in the exemplary embodiment of FIG. 1, gripper 104 is supporting pipette tip flat 106. In the exemplary embodiment of FIG. 1, second gripper arm 114 includes a retainer clip bevel 116.

Pipette tip flat 106 may include a plurality of pipette tips 130 and a plate 132 that supports the plurality of pipette tips 130 upright. The plurality of pipette tips are oriented with respect to each other by plate 132. Plate 132 may be a tip holding card, tray, cassette, rack, or the like. In an exemplary process, the controller of pipetter instrument 100 sends a movement command to robotic arm 102 to move gripper 104 in the direction of a pipette tip rack to pick-up pipette tip flat 106. Robotic arm 102 moves toward the pipette tip rack until it is positioned above pipette tip flat 106. Robotic arm 102 moves down toward pipette tip flat 106. A sensor determines that pipette tip flat 106 is in an appropriate position to grip pipette tip flat 106, and the actuator closes one or more of the gripper arms to hold pipette tip flat 106. The controller sends a movement command to robotic arm 102 to move pipette tip flat 106 for loading on tip loading assembly 108.

Tip loading assembly 108 may include a tip depot 140, a base 142, a first retainer clip 144, and a clamping module 148. Tip depot 140 may moveably or fixedly mount to base 142. In an alternative embodiment, tip depot 140 may not mount to base 142. In the exemplary embodiment of FIG. 1, tip depot 140 moveably mounts to base 142. Clamping module 148 fixes tip depot 140 in base 142 during tip attachment thereby maintaining tip depot 140 in the proper orientation and position. In alternative embodiments, tip loading assembly 108 may not include clamping module 148.

First retainer clip 144 mounts to tip depot 140 and retains plate 132 in place after loading of tip loading assembly 108 with pipette tip flat 106. Tip depot 140 includes an insertion surface 146 that includes a plurality of receptacles 434 into which the plurality of pipette tips 130 are inserted. The insertion surface may be integral or non-integral with tip depot 140. The size, number, and orientation of the plurality of receptacles 434 may vary depending on the type of pipette tip, the type of pipette tip flat, and/or the pipetter instrument 100 utilized. For example, pipette tip flats having 96 or 384 pipette tips typically are used in multichannel pipettors such as the Beckman Multimek®. The pipette tips may or may not be disposable and may be formed of a variety of suitable materials known in the art both now or in the future including metal and plastic.

Tip loading assembly 108 provides a location for the placement of pipette tip flat 106 before attachment to pipetter 110. In the exemplary embodiment of FIG. 1, pipetter 110 includes a pipetter head 150. After alignment of pipette tip flat 106 with tip depot 140 and insertion of the plurality of pipette tips 130 into the plurality of receptacles 434, robotic arm 102 releases pipette tip flat 106. The plurality of receptacles 434 may include a beveled surface to provide additional clearance for the acceptance of misaligned tips. The controller sends a movement command to robotic arm 102 to move away from tip loading assembly 108 leaving pipette tip flat 106 in tip depot 140 as shown with reference to FIG. 2.

Figure 2:
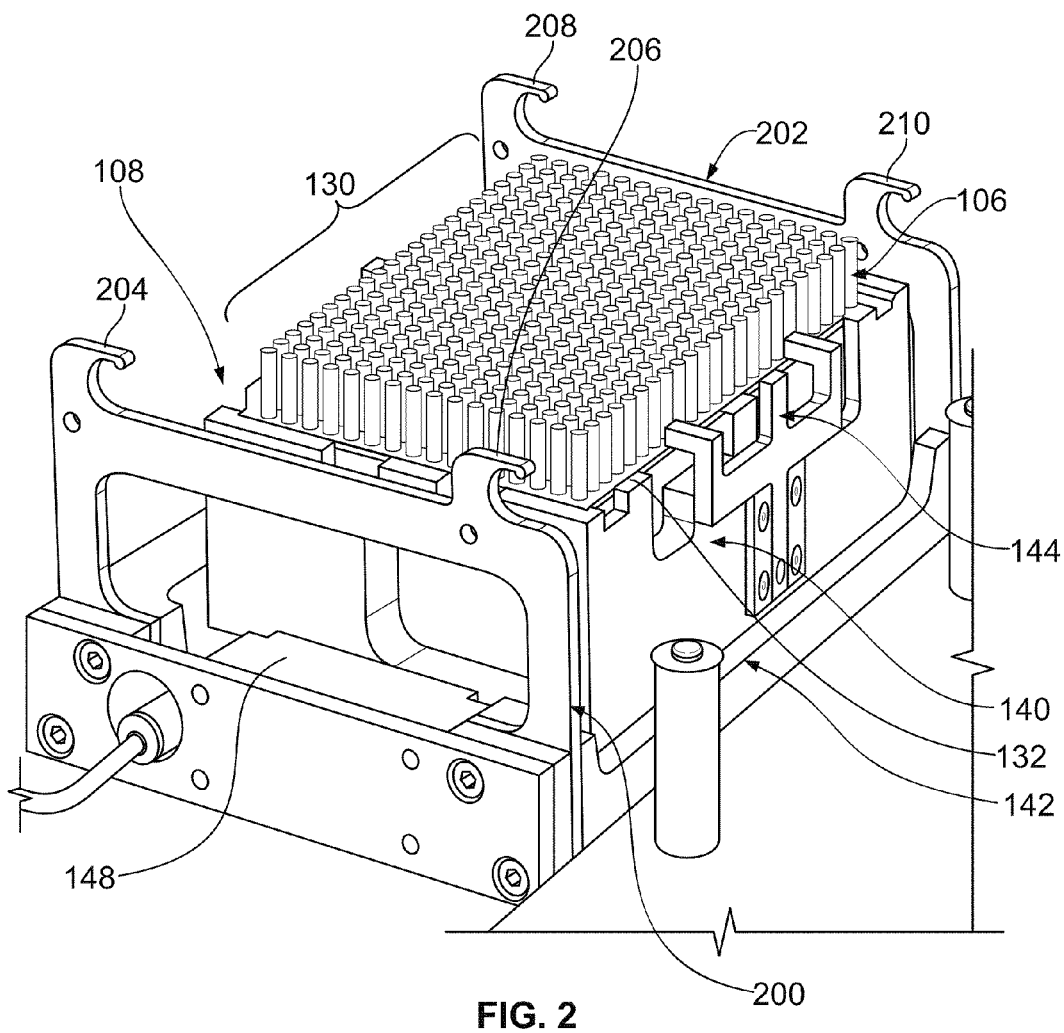
FIG. 2 is a perspective view of a tip loading assembly after loading of pipette tip in accordance with an exemplary embodiment.
Figure 3:
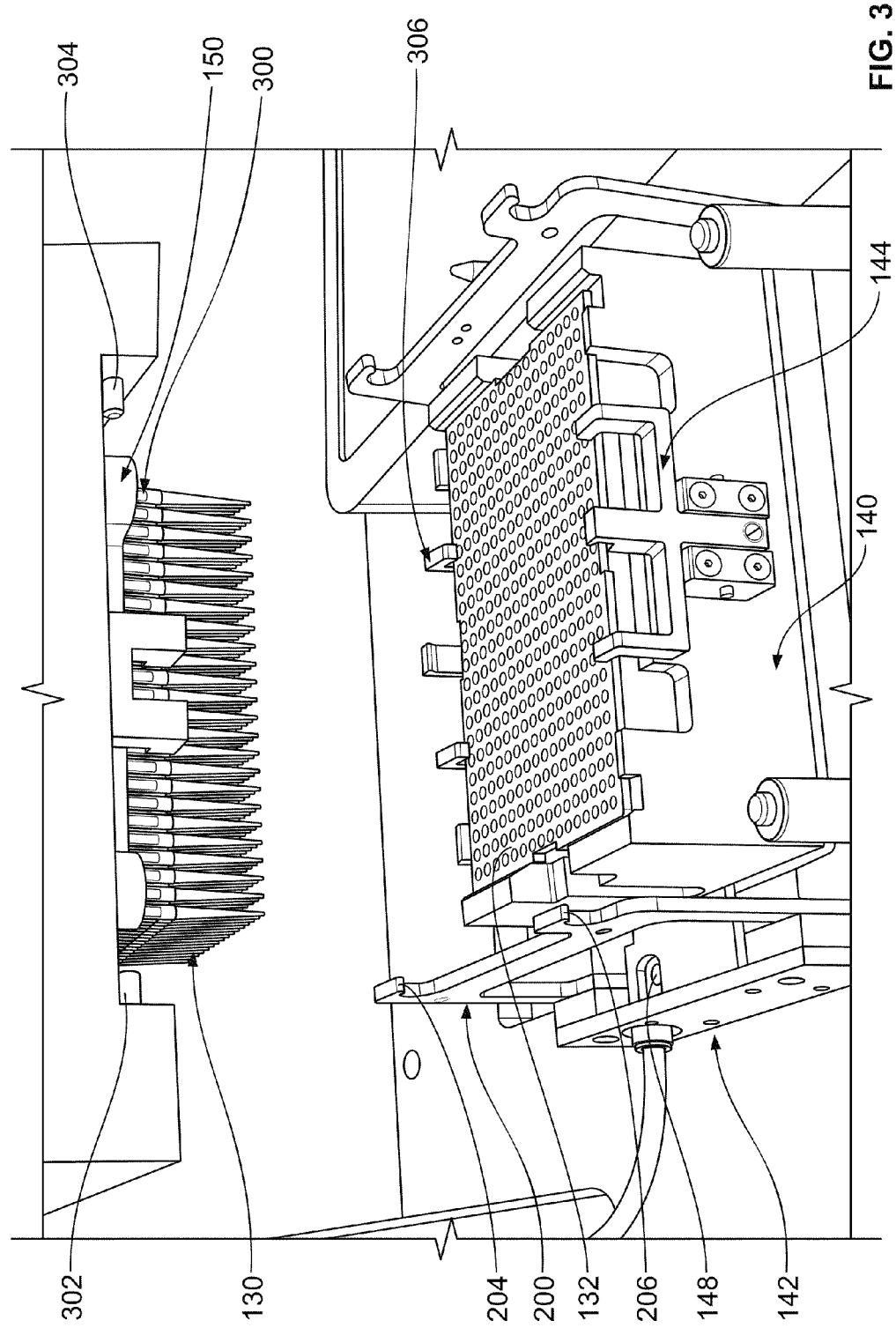
FIG. 3 is a perspective view of a pipetter after pipette tip attachment in accordance with an exemplary embodiment.

In the exemplary embodiments of FIGS. 1-3, base 142 includes a first side panel 200 and a second side panel 202. In an alternative embodiment, base 142 does not include first side panel 200 and/or second side panel 202. First side panel 200 includes a first mounting hook 204 and a second mounting hook 206 that each extend from the top of first side panel 200. Second side panel 202 includes a third mounting hook 208 and a fourth mounting hook 210 that each extend from the top of second side panel 202. The controller sends a movement command to pipetter 110 to position pipetter head 150 adjacent first side panel 200 and second side panel 202. The controller sends an engagement command to pipetter 110 to engage base 142 with pipetter head 150 so that the plurality of pipette tips 130 can be force fit onto a plurality of mandrels 300 of pipetter 110, as shown with reference to FIG. 3.

In the exemplary embodiments of FIGS. 1-3, pipetter head 150 includes a first guide pin 302, a second guide pin 304, a third guide pin (not shown), and a fourth guide pin (not shown) that each engage with one of the mounting hooks 204, 206, 208, 210. Thus, first guide pin 302, second guide pin 304, the third guide pin, and the fourth guide pin engage the mounting hooks 204, 206, 208, 210 of base 142 thereby providing support to tip depot 140 during attachment of the plurality of pipette tips 130 onto the plurality of mandrels 300 of pipetter 110. Clamping module 148 holds tip depot 140 in the proper position and orientation before, during, and after attachment of the plurality of pipette tips 130. Pipetter head 150 may have different configurations as known to those skilled in the art both now and in the future.

After the plurality of pipette tips 130 are attached to the plurality of mandrels 300, pipetter head 150 moves upward with the attached pipette tips leaving plate 132 on insertion surface 146 of tip depot 140. First retainer clip 144 and a second retainer clip 306 provide sufficient retention force to retain plate 132 on insertion surface 146 of tip depot 140. First retainer clip 144 may be wider than those utilized with prior art tip loaders to provide more even distribution of the retention force along the length of plate 132. Additionally, first retainer clip 144 may include a biasing member that provides a higher retention force than those utilized with prior art tip loaders. For example, first retainer clip 144 may include a spring having a higher spring constant to increase the retention force on plate 132.

With reference to FIG. 4, a side perspective view of tip depot 140 is shown in accordance with an exemplary embodiment. Tip depot 140 includes insertion surface 146 supported by an exemplary frame 400. In the exemplary embodiment of FIG. 4, frame 400 includes a first wall 402, a second wall 404, a third wall 406, and a fourth wall 408. The walls 402, 404, 406, 408 form a box shaped frame, although other polygonal, circular, and elliptical shaped frames may be utilized as well as frames having solid, hollow, mesh or other type walls so long as the frame is sufficiently strong to support the engagement or loading force of the tips to the mandrels. First wall 402 includes a top edge 410 proximal insertion surface 146. Second wall 404 includes a top edge 414 proximal insertion surface 146. Third wall 406 includes a top edge 418 proximal insertion surface 146. Fourth wall 408 includes a top edge 422 proximal insertion surface 146. The top edges 410, 414, 418, 422 of walls 402, 404, 406, 408 may extend slightly above insertion surface 146 forming a lip that extends above at least a portion of the peripheral edge of insertion surface 146. Insertion surface 146 extends between walls 402, 404, 406, 408 in a plane A-B.

A first gripper notch 412 extends from top edge 410 of first wall 402 and is shaped to accommodate placement of first gripper arm 112 adjacent insertion surface 146. A second gripper notch 416 extends from top edge 414 of second wall 404 and is shaped to accommodate placement of second gripper arm 114 and of first retainer clip 144 adjacent insertion surface 146. Second gripper notch 416 may include a post channel (not shown) shaped to accommodate a post 608 of first retainer clip 144, and a pivot pin receptacle (not shown) formed in a surface within the post channel. A third gripper notch 420 extends from top edge 418 of third wall 406 and is shaped to accommodate placement of the third gripper arm adjacent insertion surface 146. A fourth gripper notch 424 extends from top edge 422 of fourth wall 408 and is shaped to accommodate placement of the fourth gripper arm and of second retainer clip 306 adjacent insertion surface 146. Fourth gripper notch 424 may include a post channel 430 shaped to accommodate post 608 of second retainer clip 306. A pivot pin receptacle 432 extends from a surface within post channel 430.

The plurality of receptacles 434 are formed in insertion surface 146 to support the plurality of pipette tips upright although alternative loading directions are possible. Thus, the plurality of receptacles, for example, may be oriented to one side for loading. Each receptacle is defined by a peripheral edge 436 that defines an opening in insertion surface 146 with a dimension sufficient to accommodate, for example, the pipette tip. The peripheral edge may form a variety of shapes including polygonal, circular, elliptical, or the like. In an exemplary embodiment, peripheral edge 436 is generally circular.

With reference to FIG. 5, a side cross sectional view of insertion surface 146 is shown in accordance with an exemplary embodiment. Each receptacle of the plurality of receptacles 434 may include a beveled surface 500 and a receptacle wall 502. Beveled surface 500 extends from peripheral edge 436 of insertion surface 146. Beveled surface 500 may extend from only a portion of peripheral edge 436. Receptacle wall 502 extends from beveled surface 500 opposite peripheral edge 436. Receptacle wall 502 generally extends perpendicular to insertion surface 146 to form a cylinder. However, receptacle wall 502 need not be perpendicular and, for example, may form a cone. Receptacle wall 502 may extend from only a portion of beveled surface 500. Use of beveled surface 500 enlarges each receptacle of the plurality of receptacles 434 providing additional clearance for the acceptance of misaligned tips. For example, a beveled width 504 may be ~3.5 millimeter (mm); whereas a wall width 506 may be ~3.4 mm. Additionally, beveled surface 500 assists in directing each pipette tip of the plurality of pipette tips 130 toward the center of each receptacle of the plurality of receptacles 434.

Figure 6:
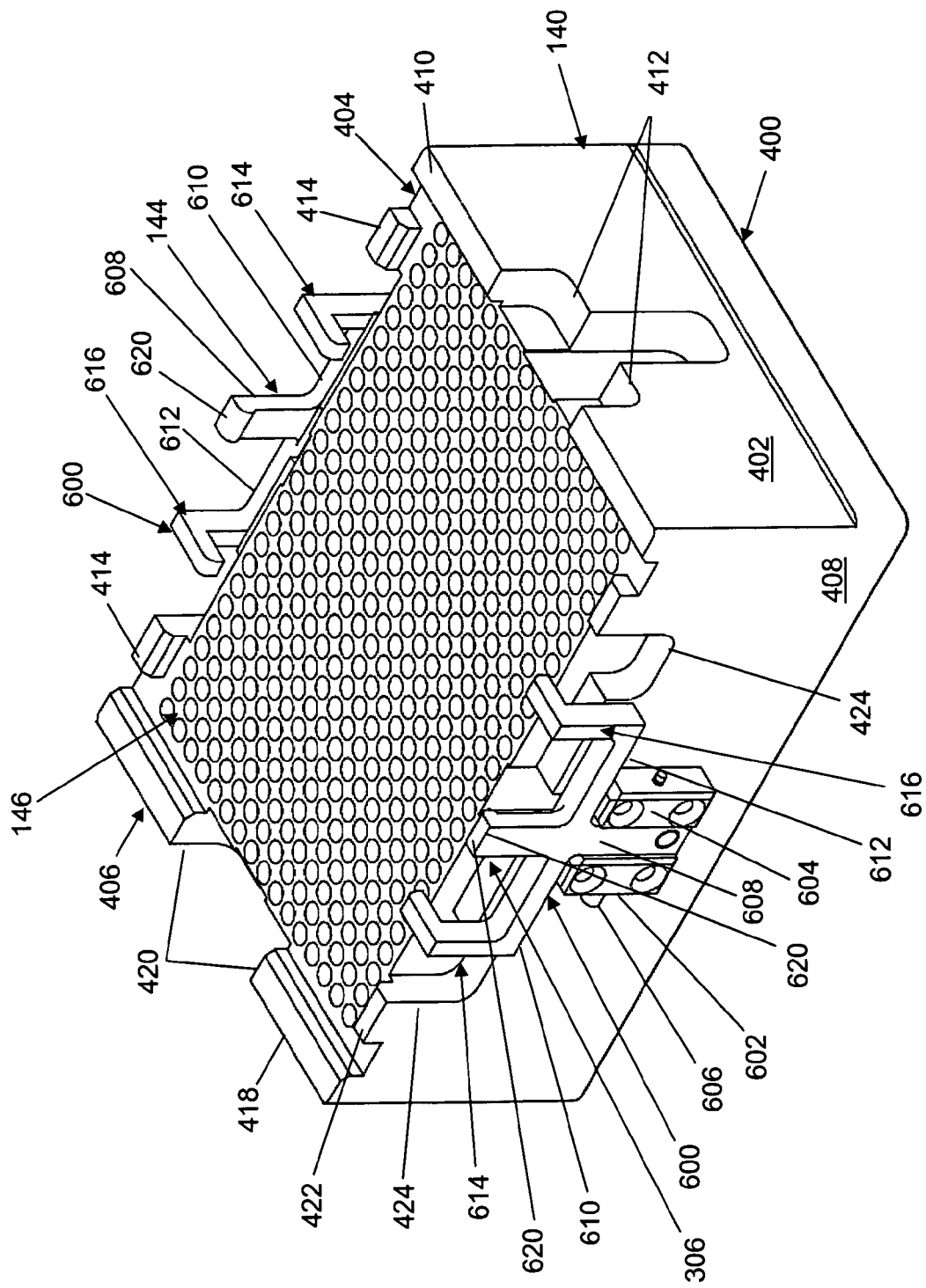
FIG. 6 is a perspective view of the tip depot of FIG. 4 including retainer clips in accordance with an exemplary embodiment.

With reference to FIG. 6, a side perspective view of tip depot 140 is shown, in accordance with an exemplary embodiment, with first retainer clip 144 and second retainer clip 306 mounted thereon. In the exemplary embodiments, first retainer clip 144 and second retainer clip 306 are comprised of retainer clip 600. Retainer clip 600 mounts to tip depot 140 using a first attachment member 602 and a second attachment member 604 that mount to tip depot 140, for example, using screws. An attachment pin 606 extends through first attachment member 602, post 608 of retainer clip 600, and a second attachment member 604 to mount retainer clip 600 to attachment members 602, 604, which mount to tip depot 140. Alternative mounting means may be used as known to those skilled in the art both now and in the future to mount retainer clip 600 to tip depot 140.

Retainer clip 600 may include post 608, a first arm 610, a second arm 612, a first hook 614, a second hook 616, a first end 618, and a contact surface 620. First arm 610 extends in a generally perpendicular direction from a first side surface of post 608. In an alternative embodiment, first arm 610 may extend at an angle from the first side surface of post 608 or any other structural arrangement that can achieve the purpose of providing contact points between the hook(s) and an item resting on the insertion surface, such as a plate, the hook(s) contacting from above, and retaining the item at rest. Second arm 612 extends in a generally perpendicular direction from a second side surface of post 608 generally opposite the first side surface. In an alternative embodiment, second arm 612 may extend at an angle from the second side surface of post 608. First hook 614 extends in a generally perpendicular direction from a side surface of first arm 610 with the extension of the hook opening toward and above insertion surface 146. Second hook 616 extends in a generally perpendicular direction from a side surface of second arm 612 with the extension of the hook opening toward and above insertion surface 146. In an exemplary embodiment, post 608 is centered between first hook 614 and second hook 616. In alternative embodiments, post 608 may be located anywhere between first hook 614 and second hook 616.

Contact surface 620 is formed at first end 618 of post 608 above insertion surface 146. Contact surface 620 may be beveled to slope downward toward insertion surface 146. In an exemplary embodiment, retainer clip bevel 116 of gripper 104 contacts contact surface 620 of retainer clip 600 as robotic arm 102 lowers gripper 104 toward insertion surface 146 pushing retainer clip 600 away from tip depot 140 thereby allowing insertion of the plurality of pipette tips 130 into the plurality of receptacles 434. As a result, post 608 preferably extends above first hook 614 and second hook 616 relative to insertion surface 146. First hook 614 and second hook 616 may include a beveled surface at an end of each hook. First hook 614 and second hook 616 extend above plate 132 after loading of the pipette tip flat 106.

With reference to FIG. 7, a side perspective view of retainer clip 600 is shown in accordance with an exemplary embodiment. Retainer clip 600 further may include a second pivot pin receptacle 700 and an attachment pin receptacle 702. Second pivot pin receptacle 700 is provided near an end of post 608 opposite first end 618 to provide a pivot point at which retainer clip 600 pivots away from tip depot 140 when retainer clip bevel 116 of gripper 104 contacts contact surface 620. Attachment pin receptacle 702 provides an opening for insertion of attachment pin 606 to mount retainer clip 600 to attachment members 602, 604.

In an exemplary embodiment, first hook 614 may include a first extension 704 and a second extension 706. First extension 704 of first hook 614 extends generally parallel to post 608 in the direction of first end 618 although this is not required. Second extension 706 of first hook 614 forms the hook that extends toward and above insertion surface 146. Similarly, second hook 616 may include a first extension 708 and a second extension 710. First extension 708 of second hook 616 extends generally parallel to post 608 in the direction of first end 618 although this is not required. Second extension 710 of second hook 616 forms the hook that extends toward and above insertion surface 146. A length of second extensions 706, 710 is selected to provide sufficient clearance for plate 132 when retainer clip 600 is in an "open" position that allows loading or unloading of the plurality of pipette tips 130.

Retainer clip 600 may include other shapes as known to those skilled in the art both now and in the future. For example, in an alternative embodiment, first arm 610 and second arm 612 may extend from post 608 at or near first end 618 forming a more generally T-shaped body. First hook 614 and second hook 616 may include second extensions 706, 710 that extend directly from first arm 610 and second arm 612. In still another alternative embodiment, a single hook surface may extend along the length of first arm 610 and of second arm 612. In still another alternative embodiment, a second extension 706 extends from a first post including a contact surface 620 thereby forming a first alternative hook. A second extension 710 extends from a second post including a contact surface 620 thereby forming a second alternative hook. The first post and the second post may be similar to post 608. In this arrangement, post 608 between the first alternative hook and the second alternative hook may not be needed. In still another alternative embodiment, first hook 614 may extend from a first post and second hook 616 may extend from a second post. First hook 614 and second hook 616 extend over insertion surface 146 limiting the vertical movement of pipette tip flat 106 after placement on tip loading assembly 108.

With reference to FIG. 8, a side view of retainer clip 600 is shown, in accordance with an exemplary embodiment, with first hook 706 and second hook 710 extending out of the page. An item 800, such as a plate, to be retained by retainer clip 600 is shown having an item dimension 802 measured along the axis A of plane A-B defined for the surface of insertion surface 146. Item dimension 802 may be a length or a width of item 800 without limitation and may alternatively extend along the axis B of plane A-B. In the exemplary embodiment of FIG. 8, a first edge 806 of second extension 706 of first hook 614 is an extremity of second extension 706 along axis A. A second edge 808 of second extension 710 of second hook 616 is an extremity of second extension 710 along axis A. A retainer clip arm extent 804 defines the distance between first outside edge 806 and second outside edge 808.

Increasing the retainer clip arm extent 804 ($L_a$) relative to item dimension 802 ($L_i$) decreases the occurrence of plate retention failures because the retention force on item 800 is more evenly distributed along the dimension of item 800. As a result, $L_a/L_i \geqq 0.33$ provides improved retention performance of tip loading assembly 108. In an exemplary embodiment wherein item 800 comprises a tip holding card, item dimension 802 is approximately 112 mm. As a result, a retainer clip arm extent 804 of greater than or equal to approximately 36 mm provides improved retention of item 800 by retainer clip 600. Separating first hook 614 and second hook 616 by ⅓ of the distance from either end of tip holding card and from each other provides the most uniform distribution of the contact force and minimizes flexing of the card. Each hook provides a contact point or contact surface on the tip holding card. For N hooks or contact points, an even distribution of the retention force is provided by $L_d/L_i \cong 1/(N+1)$.

With reference to FIG. 9, a side perspective view of a pivot pin 900 is shown in accordance with an exemplary embodiment. Pivot pin 900 may include a base 902 and a head 904. In an exemplary embodiment, pivot pin 900 has a generally cylindrical shape with a circular cross section although other polygonal shapes are possible. Base 902 mounts within second pivot pin receptacle 700 of retainer clip 600. Head 904 extends from base 902 and may have a larger cross sectional diameter than base 902 that does not mount within pivot pin receptacle 700 of retainer clip 600.

Figure 10:
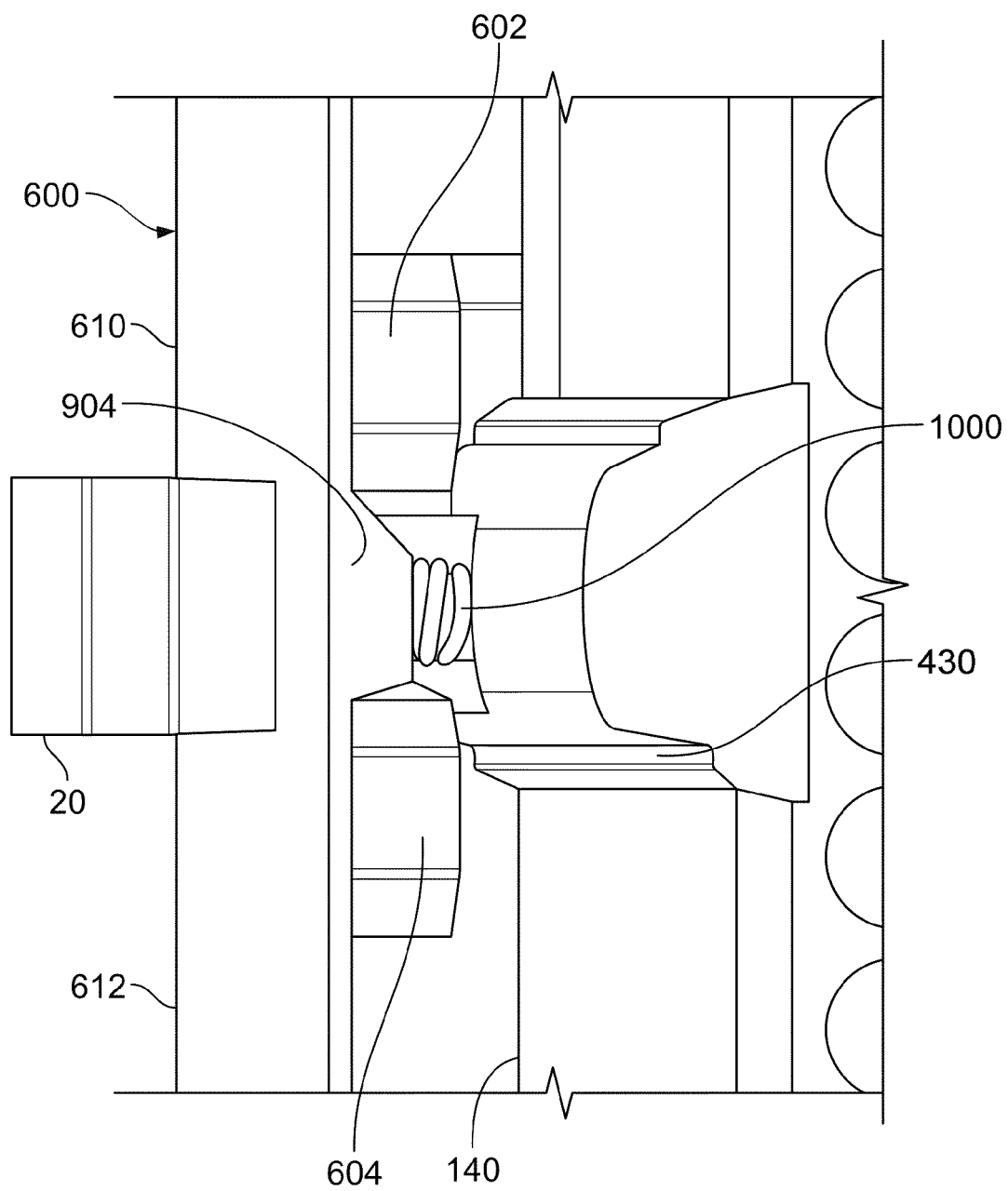
FIG. 10 is a perspective view of the retainer clip of FIG. 7 in an "open" position in accordance with an exemplary embodiment.

With reference to FIG. 10, a view of retainer clip 600 pivoted away from tip depot 140 is shown in accordance with an exemplary embodiment. A biasing member 1000 extends between head 904 of pivot pin 900 and pivot pin receptacle 432 of tip depot 140. In the exemplary embodiment of FIG. 10, biasing member 1000 comprises a spring biased in a "closed" or non-pivoted position so that contact between retainer clip bevel 116 of gripper 104 and bevel contact surface 618 of retainer clip 600 forces retainer clip 600 away from tip depot 140 against the force of biasing member 1000. In an exemplary embodiment, the spring has a spring constant of approximately 2.1 Newtons/millimeter (N/mm) (e.g. 2.08 N/mm in one embodiment) as compared with prior art devices, which utilize a spring having a spring constant of approximately 0.61 N/mm. The increased biasing force also decreases the occurrence of plate retention failures. However, the necessary force can vary depending on the material from which the plate is made and the surface area of contact between the plate resting on the insertion surface and the hook(s). One of skill in the art will understand that while embodiments are illustrated herein having the biasing force provided by a spring, any other suitable actuator can be employed to provide the biasing force. For example, a pneumatic, electromechanical, or other actuator may be used to provide the biasing force to maintain the plate in place on the insertion surface.

Figure 11:
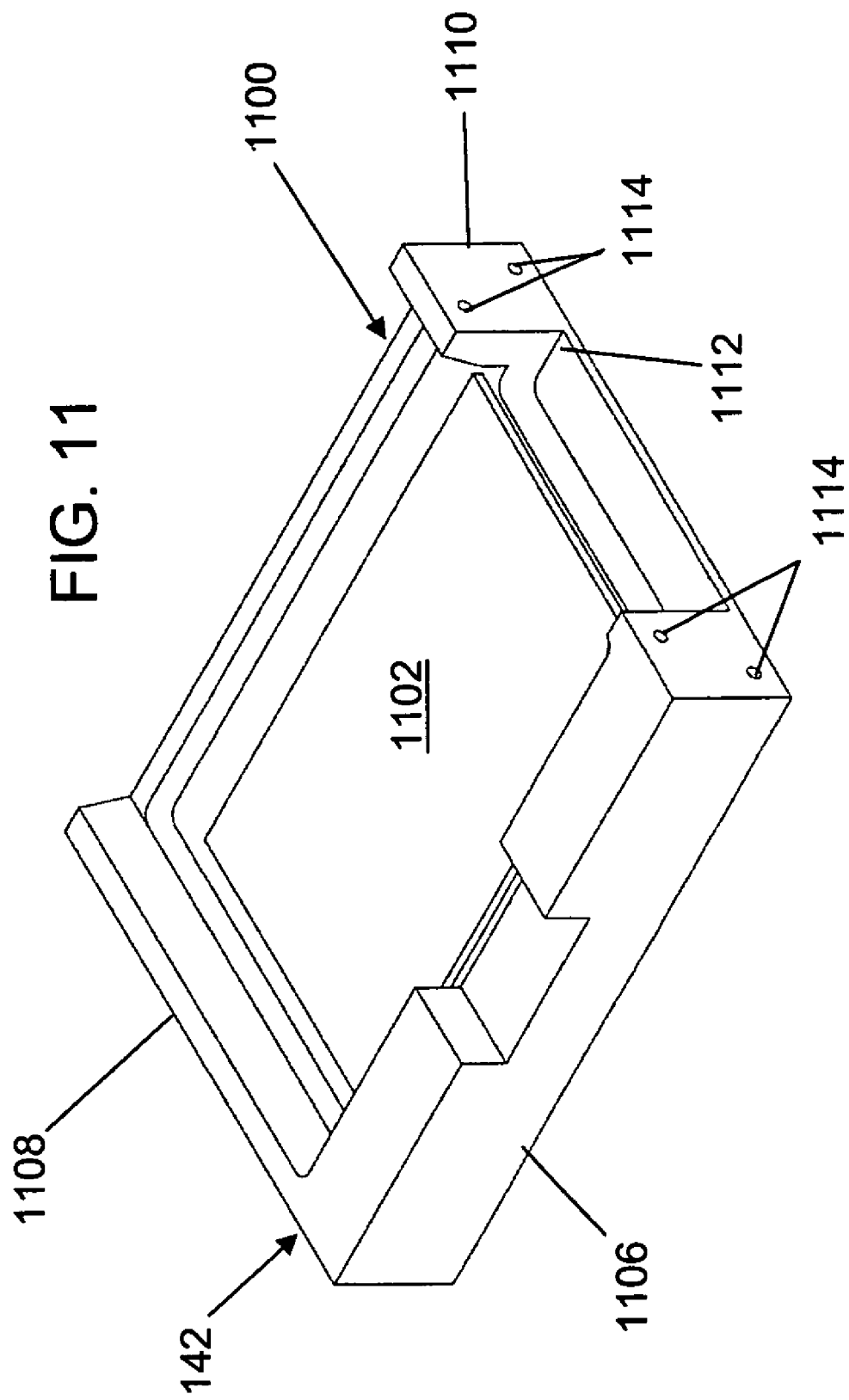
FIG. 11 is a perspective view of a base of the tip loading assembly of FIG. 2 in accordance with an exemplary embodiment.

With reference to FIG. 11, a perspective view of base 142 without first side panel 200 and/or second side panel 202 is shown in accordance with an exemplary embodiment. Base 142 may include a base plate 1102 and a shim 1104. Base plate 1102 provides a bottom surface for supporting tip depot 140. In the exemplary embodiment of FIG. 11, base plate 1102 has a generally planar, rectangular shape although other polygonal and elliptical shapes are possible. Shim 1104 extends from at least a portion of base plate 1102 in a generally perpendicular direction. In the exemplary embodiments, shim 1104 may include a rear shim 1106, a first side shim 1108, and a second side shim 1110. Second side shim 1110 may include a clamping module notch 1112 and a plurality of bracket pin receptacles 1114. Shim 1104 provides the proper spacing between base 142 and tip depot 140. One or more shim may be removably mounted to base plate 1102 based on the type of tip depot utilized. Different tip depot types may be utilized to accommodate different numbers and/or sizes of pipette tips.

Figure 12:
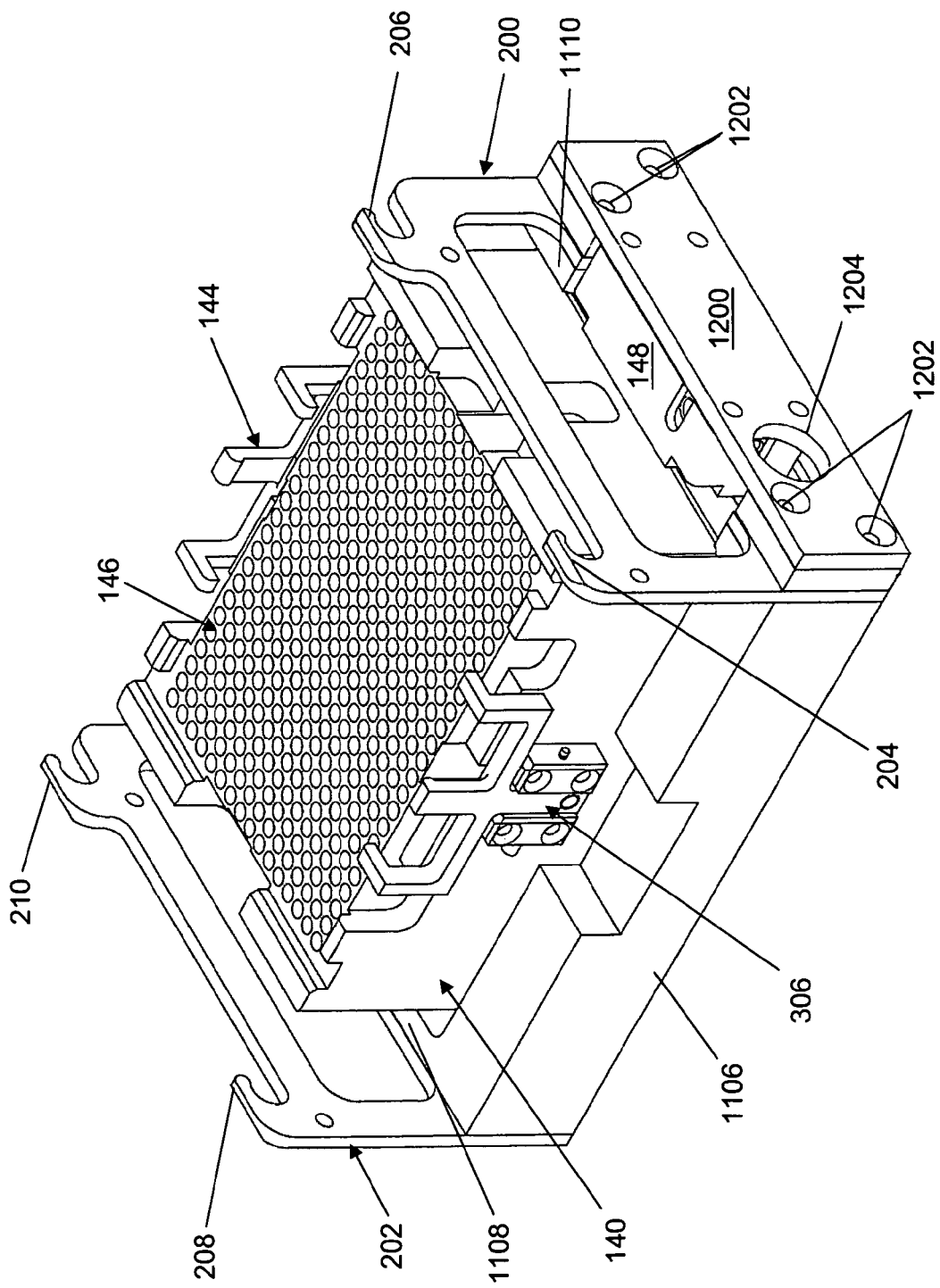
FIG. 12 is a second perspective view of the tip loading assembly of FIG. 2 in accordance with an exemplary embodiment.

With reference to FIG. 12, a perspective view of tip depot 140 resting on base 142 is shown in accordance with an exemplary embodiment. First side panel 200 and second side panel 202 mount to first side shim 1108 and to second side shim 1110, respectively. Base 142 further may include a mounting bracket 1200, and a plurality of mounting pins 1202. Clamping module 148 may mount to mounting bracket 1200. Mounting bracket 1200 provides the appropriate spacing between clamping module 148 and tip depot 140. Mounting bracket 1200 is mounted to base 142 using the plurality of mounting pins 1202 inserted into the plurality of bracket pin receptacles 1114 of base 1100.

Clamping module 148 may include a clamp (not shown). In the exemplary embodiment of FIG. 12, clamping module 148 mounts to mounting bracket 1200. In other exemplary embodiments, clamping module 148 may mount directly to second side shim 1110, to first side shim 1108, to base plate 1102, and/or to rear shim 1106. In the exemplary embodiment of FIG. 12, an actuator (not shown) housed within clamping module 148 causes the clamp to extend toward tip depot 140 fixing tip depot 140 in position in base 142 to receive or attach the plurality of pins 130. The actuator may be any device as known to those skilled in the art both now and in the future for causing movement of the clamp. Exemplary actuators include an electric motor, a servo, stepper, or piezo motor, a pneumatic actuator, a gas motor, or the like. An example commercial clamping module that may be utilized is a Type No. EV-15/40-4, Part No. 13289, manufactured by Festo Corporation. Other clamping modules capable of maintaining the proper position and orientation of tip depot 140 may be used as known to those skilled in the art both now and in the future. For example, a bolt-screw mechanism mounted on base 142 may be used.

In an exemplary embodiment, clamping module 148 is pneumatically driven through a solenoid installed in pipetter 110. The controller can toggle clamping module 148 on and off to engage or to disengage tip depot 140 through a force exerted normal to a wall of tip depot 140. Tip depot 140 should remain level during clamp engagement. When clamp 1302 disengages, tip depot 140 can move freely back and forth along clamp 1302.

Retention of tip holding cards 132 on a plurality of pipette tips 130 after attachment to pipetter head can create system failures and hazards despite manufacturer quality control attempts to improve pipette tips and pipette tip flats. Tip loading assembly 108 includes improvements that ensure sufficient retention force by retainer clip 600, that ensure misaligned pipette tips can be properly loaded into tip loading assembly 108, and that maintain the proper tip depot position and orientation before, during, and after tip attachment to the plurality of mandrels 300 of pipetter head 150 thereby reducing the probability of a tip attachment failure.

The foregoing description of exemplary embodiments of the invention have been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method for loading a plurality of pipette tips on a plurality of mandrels of a pipetter, the plurality of pipette tips oriented with respect to each other by a plate, the method comprising:

providing a pipettor and a loading assembly comprising an insertion surface including a plurality of receptacles configured to accept the plurality of pipette tips, a receptacle of the plurality of receptacles including a beveled surface extending from at least a portion of the insertion surface; and a plate supporting the plurality of pipette tips;

inserting the plurality of pipette tips in the plurality of receptacles of the insertion surface;

attaching the plurality of pipette tips to a plurality of mandrels of the pipettor;

applying a retention force to the plate by a retainer clip mounted in the tip loading assembly to maintain the plate on the insertion surface; and separating the plurality of pipette tips attached to the plurality of mandrels from the plate;

wherein the retainer clip comprises:
a post;
an arm extending from the post in a first direction;
a first hook extending from the arm over a first portion of the plate, the first hook including a first edge; and
a second hook extending from the arm over a second portion of the plate, the second hook including a second edge;

wherein $L_a$ is a distance between the first edge and the second edge, wherein $L_i$ is a dimension of the plate along an axis extending between the first edge and the second edge, and further wherein the ratio of $L_a$ over $L_i$ is approximately greater than or equal to 0.33.

2. The method of claim 1, further comprising the step of supporting the insertion surface on a plurality of walls extending upward from a base of the loading assembly.

* * * * *